United States Patent
Worsoee

(10) Patent No.: US 7,313,832 B2
(45) Date of Patent: Jan. 1, 2008

(54) OSTOMY SUPPORT GARMENT

(75) Inventor: Bjarne Worsoee, Tikoeb (DK)

(73) Assignee: Coloplast A/S, Humlebaek (DK)

( * ) Notice: Subject to any disclaimer, the term of this patent is extended or adjusted under 35 U.S.C. 154(b) by 10 days.

(21) Appl. No.: 10/542,363

(22) PCT Filed: Feb. 3, 2004

(86) PCT No.: PCT/DK2004/000075

§ 371 (c)(1),
(2), (4) Date: Jul. 14, 2005

(87) PCT Pub. No.: WO2004/069118

PCT Pub. Date: Aug. 19, 2004

(65) Prior Publication Data
US 2006/0189952 A1    Aug. 24, 2006

(30) Foreign Application Priority Data
Feb. 3, 2003    (DK) .............................. 2003 00143

(51) Int. Cl.
*A41B 9/00* (2006.01)
*A61F 5/44* (2006.01)

(52) U.S. Cl. .......................... 2/400; 604/345; 604/335; 2/114

(58) Field of Classification Search ............ 2/400–406, 2/114; 604/345, 335
See application file for complete search history.

(56) References Cited

U.S. PATENT DOCUMENTS

| | | | | |
|---|---|---|---|---|
| 3,468,310 A | * | 9/1969 | Kimball | 604/345 |
| 4,495,662 A | * | 1/1985 | Miller | 2/211 |
| 4,533,355 A | * | 8/1985 | Fair | 604/345 |
| 4,888,006 A | * | 12/1989 | Beaupied | 604/345 |
| 5,135,520 A | * | 8/1992 | Beaupied | 604/345 |
| 5,248,308 A | | 9/1993 | von Emster | |
| 5,626,570 A | | 5/1997 | Gallo | |
| 5,843,054 A | * | 12/1998 | Honig | 604/345 |
| 6,014,777 A | | 1/2000 | Gupton | |
| 6,202,222 B1 | * | 3/2001 | Robbins | 2/406 |
| 6,468,254 B2 | * | 10/2002 | Gupton | 604/345 |
| 6,635,050 B1 | | 10/2003 | Jensen et al. | |
| 2002/0016578 A1 | | 2/2002 | Gupton | |

FOREIGN PATENT DOCUMENTS

| | | |
|---|---|---|
| DE | 100 51 080 C1 | 3/2002 |
| DK | 174536B B1 | 5/2003 |
| WO | WO 00/67683 | 11/2000 |

* cited by examiner

*Primary Examiner*—Gloria M. Hale
(74) *Attorney, Agent, or Firm*—Jacobson Holman PLLC

(57) ABSTRACT

An ostomy support garment in the form of a material having a hole for receiving a stoma. The hole has a stabilized edge that is provided with an element allowing an increase or reduction of the length of the edge of the hole to obtain a snug fit to the stoma. This also ensures an easy application and removal of the garment and of a collecting bag combined with a sufficient support next to the stoma.

7 Claims, 2 Drawing Sheets

OSTOMY SUPPORT GARMENT

This is a nationalization of PCT/DK2004/000075 filed 3 Feb. 2004 and published in English.

BACKGROUND OF THE INVENTION

1. Field of the Invention

The present invention relates to an ostomy support garment having a hole for receiving a stoma and more particularly to an ostomy support garment having an adjustable hole for receiving a stoma.

In connection with surgery for a number of diseases in the gastrointestinal tract, in many cases a consequence is that the colon, the ileum or the urethra has been exposed surgically and the patient is left with an abdominal stoma. Such artificial openings or fistulae cannot be controlled at will and are therefore of necessity incontinent and the effluents or waste products of the body, which are conveyed through these organs, are discharged through the artificial orifice or opening and are collected in a collection bag. The bag is usually adhered to the skin by means of an adhesive wafer or plate having an inlet opening for accommodating the stoma. Such appliances may be two-piece or one-piece appliances. In both types of appliances, a body side member is attached to the wearer's abdomen, and a receiving member or bag is attached to the body side ostomy member for receiving exudates from the stoma. The receiving member is attached releasably in the case of a two-piece appliance.

In many instances patients having had a surgery resulting in the formation of a stoma, an accompanying condition is formation of a peristomal bulge or hernia, which may complicate the bandaging of the stoma and even require further surgery. Even if further surgery is carried out there is a considerable risk of a permanent condition, which cannot be alleviated.

In such cases, the patient will have to rely on an additional hernia support for a mechanical reposition of the bulge or hernia for reducing the risk of constriction or strangulation calling for urgent surgery and for providing a plane surface around the stoma for application of a collecting appliance in order to secure a proper adherence and sealing. Stomal bulge or hernia supports are commonly known and may e.g. be in the form of a belt of e.g. of leather with buckles or in the form of a support garment made from an elastic fabric being able to apply a sufficient pressure around the stoma.

In the case of a colostomy and in case the ostomate is normally irrigating, a minor cap or collecting bag may be used which enables the use of a firm support belt or tight compression briefs for providing a sufficient pressure around the stoma. For ileostomates or urostomates this procedure is not practicable due to the constant rather high output from the ileum or bladder and for urostomates it may be critical to provide a free flow from the stoma in order to prevent a build-up of a backpressure, which may destroy the kidneys.

In such cases, it is highly desirable or mandatory to give access to a larger collecting volume, which means that the collecting bag itself will have to be situated outside the pressure establishing belt or briefs and that a passageway through the same has to be established.

Determination of the site for placing the stoma is normally carried out prior to the operation after observing the patient in different postures, e.g. sitting, standing and bending over, finding the less critical area. WO 00/67683 discloses a device for use in the determination of the optimum position of a stoma-to-be for the patient in question.

As the placing of a stoma is not standardised but depends on the condition and the topography of the abdominal area of the patient, it is not possible to provide a simple selection of standard bulge or hernia supports fitting the majority of patients. The passageways must be tailored according to the actual conditions of the individual patient.

When making a hole in an ostomy support garment it has to be considered that the supporting effect of the missing material has to be provided for in another way and furthermore, it is necessary to stabilize the edge of a hole in order to avoid that it being inadvertently enlarged. At the same time, the effect of the stretching of the support garment and deformation of the shape of the hole when applied has to be taken into consideration as well as the problems associated with providing a sufficiently large hole for allowing an easy passing of an ostomy collection bag during application and removal of the garment and the passing of intestinal contents from the stoma into the bag and at the same time providing a sufficiently snug fit to the stoma to ensure the support next to the stoma.

2. Description of the Related Art

DK Patent Application No. PA 1999 01559 discloses a stomal hernia support compression garment in the form of a pair of compression trousers having a customized hole. The edge of the hole is stabilized by incorporation of a string of nylon sewn with a lockstitch and a zigzag stitch to ensure that the shape of the hole is not changed and furthermore, an enforcement of cotton is sewn using zigzag stitch for stabilizing the area around the hole.

U.S. Pat. No. 5,135,520 discloses a variable closure device for an ostomy garment having a pair of criss-cross pocket forming panels configured to lie behind an ostomy device. The criss-cross arrangement of pocket panels are created by finished edges which overlap along their lower ends to define an adjustable, elongated, slanted slot.

It is an object of the present invention to provide a hernia supporting device which provides a hole through which an ostomy bag may be passed, but which is shaped such that the bag is not moved out of the hole by accident. Thus it is an object to provide a hole with an unbroken edge.

It is also an object of the present invention to provide a hole which is flexible so as to make it easier for the user to pass the ostomy bag through the hole and such that the hole adapts to the shape of the ostomy device.

Additionally it is an object of the present invention to provide a supporting device that has an inner surface which is as smooth as possible, such that it does not irritate the skin it is pressed against. Thus it is an object of the present invention to provide no or as few seams or overlapping materials as possible.

SUMMARY OF THE INVENTION

The present invention relates to an ostomy support garment having a hole for receiving a stoma, said hole having a stabilized and adjustable edge.

BRIEF DESCRIPTION OF THE DRAWINGS

The invention is disclosed more in detail with reference to the drawings in which.

DETAILED DESCRIPTION OF THE PRESENT INVENTION

Figure 1:
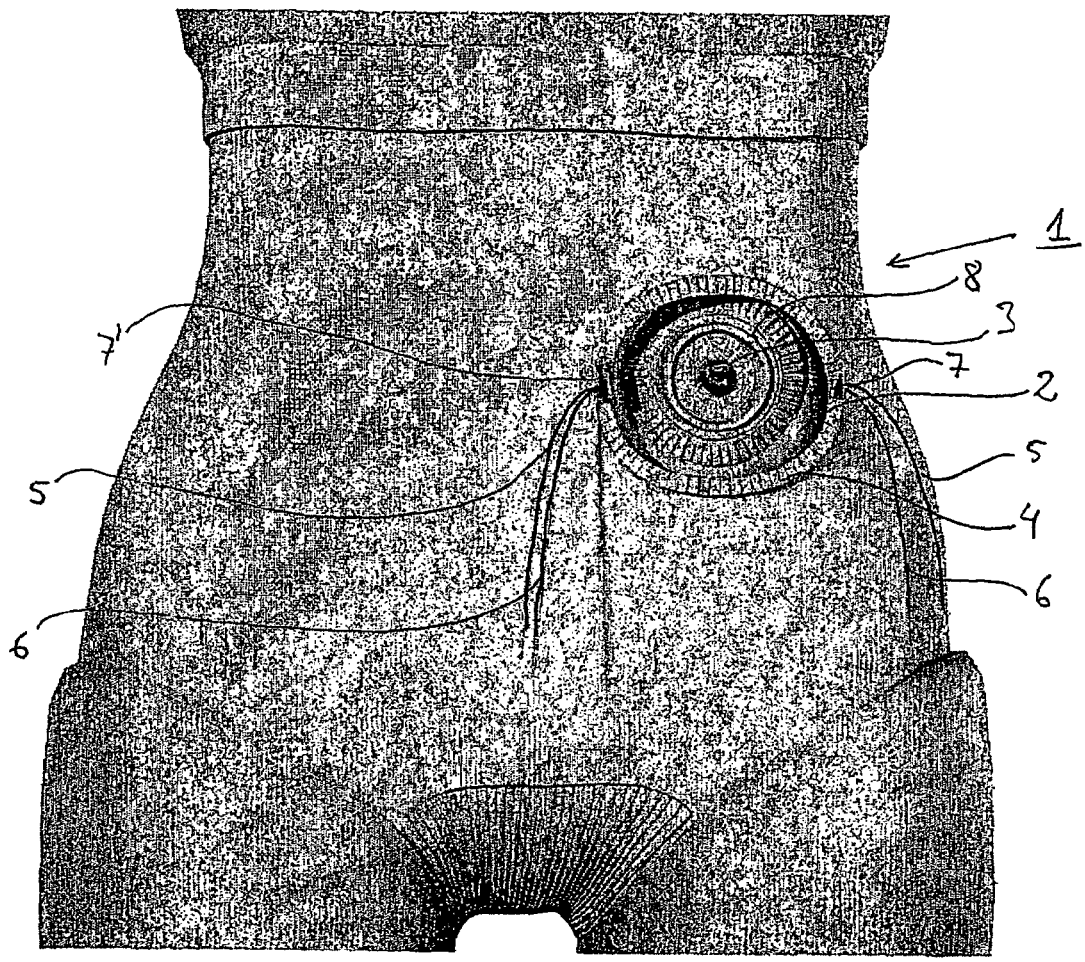
FIG. 1 shows an embodiment of the invention in the form of a pair of support briefs worn by a user.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention relates to an ostomy support garment in the form of a material having a hole for receiving a stoma, said hole having a stabilized edge wherein the edge is provided with an element allowing an increase or reduction of the length of the edge of the hole and wherein the element is a cord placed in a passage at the edge of the hole.

It may be seen as an advantage of the present invention that the hole (and its edge) is provided in one piece which is both flexible and stable enough to support the ostomy bag. Had the edge of the hole been inflexible it would be harder to pull the ostomy bag through the hole, as the hole could not be temporarily enlarged. Furthermore an unflexible hole could not follow the movement of the user and thus an edge of the hole would apply unwanted pressure to the ostomy bag for some positions of the user e.g. when sitting down or when bending forward.

It may further be seen as an advantage of the present invention that the surface surrounding the hole is provided as one piece of material whereby seams and overlapping elements are avoided. By avoiding such seams and overlaps the risk of irritation of the skin of the user is minimised.

By changing the effective length of the edge of the hole, the size of the hole may be temporarily increased and/or the shape of the hole may be temporarily changed for facilitating the application or removal of the garment or a collecting bag. By length of the edge of the hole is meant the length of the perimeter of the hole i.e. the distance along the inner edge of the hole. The cross-sectional area of the hole may be bigger by increasing the length of the edge. However for the same length of the edge of the hole, the cross-sectional area may vary as a circular hole has bigger area than an elliptic hole.

As the hole is defined by the flexibility of the garment material and the adjustability of the cord element, the cross-sectional shape of the hole may be changed by the user. E.g. the user may pull one zone of the edge in one direction and thus provide an oval shape of the hole. Due to the flexible nature of the garment the inner shape of the hole will adapt to the outer shape of the ostomy bag and thus provide a snug fit between the bag and/or a coupling provided on the bag and the hernia supporting device.

The use of a passage in the edge of the hole stabilized the edge and allows for a continuous adaptation of the length of the edge of the hole. The passage may extend along the entire edge of the hole or may be divided into a plurality of passages distributed along the edge. If a plurality of passages are provided it may be easier for the user to replace a broken cord as the user does not have to thread a cord through a long passage without being able to pull the cord most of the way. On the other hand a continuous cord provides the best fit between the device and the ostomy bag.

The garment of the invention has a hole having a stabilized edge being sufficiently stiff and providing a snug fit to the stoma to ensure a sufficient support next to the stoma and also enabling an easy application and removal of the garment or a collecting bag.

The supporting device of the present invention may be mass-produced in different sizes and with different positions of the hole. However the best fit is provided by customizing the device and the hole the user of the device. Such customization makes it possible to provide an even closer fit between the edge of the hole and the ostomy bag as the hole is positioned in the exactly the right spot.

In one embodiment the garment of the invention is made from an elastic material and the element is a string attached to the edge in a manner allowing an increase or decrease of the perimeter of the hole. When tightening the string, a snug adaptation of the size of the hole to the stoma is obtained together with a sufficient support next to the stoma and when loosening the string, an enlargement of the size of the hole is obtained which facilitates the application and removal of the garment or a collecting bag.

In one preferred embodiment of the invention the element is forming a lace giving the option of a simple fixation of the length by tying a knot or bow or by locking the ends of the cord using a cord lock when the ends of the cord have a common exit from the passage. This embodiment gives a simple loosening and fixation of the cord(s) and adaptation of the length of the rim of the hole, especially for users having poor dexterity.

In another preferred embodiment of the invention the element is in the form of two cords having two common exits from the passage, preferably situated spaced about 180° from each other, the cords passing through complementary parts of the passage and each set of two ends of the cords having the common exits from the passage being locked using a cord lock.

In an alternative embodiment, the element is an elastic element which together with the elasticity of the material from which the garment is made allows for a temporary enlargement of the hole without having to rely on untying and tying a string or lace. An elastic element is suitably an elastic band such as a band of rubber, cord fabric, or cavalry twill.

In a further embodiment of the invention the garment has a hole, which is provided with a slit, which juts from the edge of the hole into the material, and the element is a fastening element enabling a closure of the slit reducing the perimeter of the hole. When removing the fastening element temporarily, the hole may easily be enlarged and obtain a keyhole shape facilitating the application and removal of the garment or a collecting bag. Then, the fastening element is repositioned closing the slit and providing a snug fit to the stoma and a sufficient support next to the stoma. In this embodiment, the increase or reduction of the length is not depending on elasticity of the material from which the garment is made. Thus, also non-elastic materials may be used without jeopardizing the facility of the application and removal of the garment or a collecting bag.

In this embodiment, the fastening is an element closing the slit is suitably a lace placed in a passage at the edge of the hole, said passage being interrupted by the slit. When untying the lace, the hole may be enlarged and obtain a keyhole shape and the size of the hole is reduced by tying a knot or bow drawing the ends of the passage together providing a snug fit to the stoma.

In the alternative, the fastening closing the slit is a zip-like fastener drawing the edges of the slit together or snaps, buckles, buttons, rings or by mating elements of hook and loop fastening material bridging the slit at the edge of the hole.

If the fastenings closing the slit are able to take up the stretching forces of the garment when applied, the slit may stretch from the edge of the hole to the waist-line of the garment facilitating the application and removal of the garment.

DESCRIPTION OF THE PREFERRED EMBODIMENTS

The invention is now explained more in detail with reference to the drawings showing preferred embodiments of the invention.

Reference is made to FIG. 1 showing an embodiment of an ostomy support garment of the invention in the form of a pair of support briefs 1 worn by a user. The briefs have a hole 2 for receiving a stoma 3, the hole having a stabilized edge 4 wherein the edge is in the form of a passage in which are placed two cords 5, 6 leaving the passage through two common exits from the passage situated spaced about 180° from each other. Each of the cords passes through complementary parts of the passage and each set of two ends of the cords have common exits from the passage being locked using a cord lock 7,7'. An ostomy body side member 8 is placed on the abdomen of the user for attachment of a collecting bag.

Figure 2:
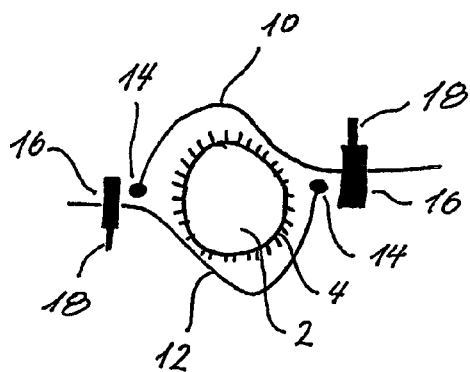
FIGS. 2-7 show different configurations of the cord arrangement and garment.
Figure 3:
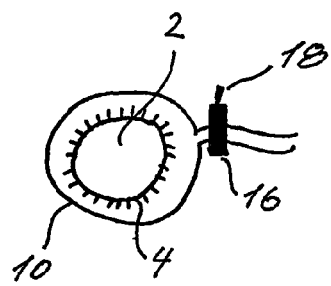
Figure 4:
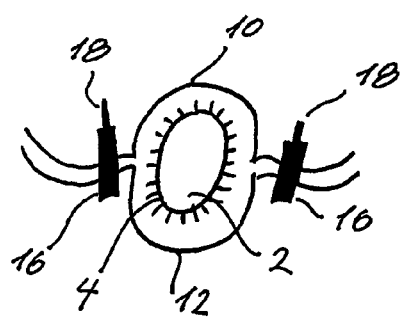

FIGS. 2-6 show different configurations of cords. In FIG. 2, a first cord 10 and a second cord 12 are each attached to a point of attachment 14. The cords together encircle the hole 2 with the stabilized edge 4. In the embodiment of the figure the cords encircles the entire hole, but in other embodiments the cords may encircle only a part of the hole 2. Each cord is tightened by means of a cord fastener 16 having a spring biased rod 18 adapted to secure the cord. In the figure the cords each encircle one half of the hole 2. However in other embodiments the cords may encircle different shares of the hole. For example, one cord may encircle one quarter of the hole while the other encircles three quarters of the hole. In the configuration of FIG. 3 only a first cord 10 is provided. The cord encircles the entire hole 2 and is tightened by means of a cord fastener 16. In FIG. 4 the hole 2 is encircled by a first cord 10 and a second cord 12. Two cord fasteners 18 are provided and each is adapted to tighten an end of the first cord 10 and an end of the second cord 12.

Figure 5:
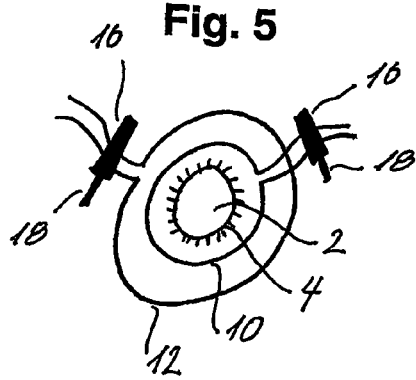
Figure 6:
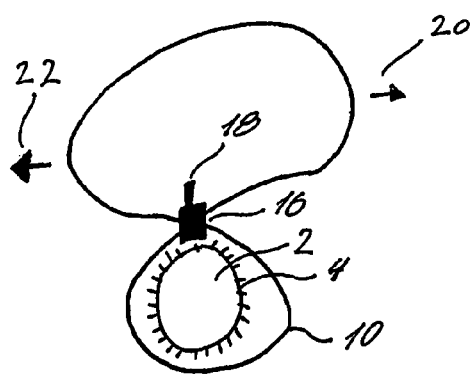

The configuration of FIG. 5 is related to the configuration of FIG. 3 but with two cords—a first cord 10 and a second cord 12—being provided. The first cord 10 is provided closer to the stabilized edge 4 than the second cord 12. In FIG. 6 a first cord 10 is provided in a figure eight shape. Thus the user of the device may close the hole by pulling the free part of the figure eight shape in opposite directions 20 and 22. The tightened cord may be released from the cord fastener 18 by means of the rod 18.

Figure 7:
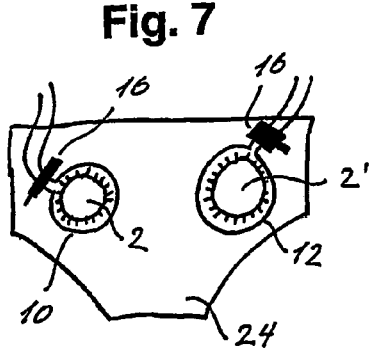

In FIG. 7 a garment is provided with two holes, each for one stoma. The holes have stabilized edges and may be fastened by means of first cord 10 and second cord 12 and their respective cord fasteners 16.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An ostomy support garment to be worn by a person with a stoma comprising an undergarment with a hole passing therethrough which is positioned to surround and expose the stoma when said undergarment is worn, said hole having an edge that defines a hole perimeter, a passage formed in said garment adjacent said edge and extending at least partly around said hole perimeter, and a string, cord or lace passed through said passage to increase and decrease said hole perimeter.

2. The ostomy support garment as claimed in claim 1 wherein the garment is made from an elastic material.

3. The ostomy support garment as claimed in claim 1 wherein the string, cord or lace is an elastic element.

4. The ostomy support garment as claimed in claim 1 wherein the string, cord or lace is made of elastic or fabric.

5. An ostomy support garment to be worn by a person with a stoma comprising an undergarment having a hole therethrough that surrounds and exposes the stoma when the undergarment is worn, said hole having an edge that defines a perimeter of said hole, a passage formed adjacent said perimeter that extends at least partly around said hole, and a string, cord or lace passed through said passage and configured to increase and decrease the hole perimeter.

6. The ostomy support garment as claimed in claim 5 wherein said garment is made of an elastic material.

7. The ostomy support garment as claimed in claim 5 wherein the string, cord or lace is made of elastic or fabric.

* * * * *